United States Patent [19]

Fischer et al.

[11] 4,332,725
[45] Jun. 1, 1982

[54] PROCESS FOR THE PREPARATION OF 1-[3-MERCAPTO-(2S)-METHYLPROPIONYL]-PYRROLIDINE-(2S)-CARBOXYLIC ACID

[75] Inventors: János Fischer; Laszlo Rózsa; Pál Vagó; Anná Bakonyi; Gábor Fázekas, all of Budapest, Hungary

[73] Assignee: Egyt Gyogyszervegyeszeti Gyar, Budapest, Hungary

[21] Appl. No.: 218,814

[22] Filed: Dec. 22, 1980

[30] Foreign Application Priority Data

Dec. 29, 1979 [HU] Hungary .............................. EE 2720

[51] Int. Cl.³ .......................................... C07D 207/16
[52] U.S. Cl. ................................................. 548/533
[58] Field of Search .......................... 260/326.2, 326.4

[56] References Cited

U.S. PATENT DOCUMENTS

| | | | |
|---|---|---|---|
| 4,105,776 | 8/1978 | Ondetti et al. | 260/326.2 |
| 4,181,663 | 1/1980 | Haugwitz et al. | 260/326.2 |
| 4,241,076 | 12/1980 | Ondetti et al. | 260/326.2 |
| 4,284,561 | 8/1981 | Petrillo et al. | 260/326.2 |
| 4,288,368 | 9/1981 | Haugwitz | 260/326.2 |
| 4,297,282 | 10/1981 | Ohashi et al. | 260/326.2 |

FOREIGN PATENT DOCUMENTS 2039478  8/1980  United Kingdom ............. 260/326.2

Primary Examiner—Mary C. Lee
Attorney, Agent, or Firm—Karl F. Ross

[57] ABSTRACT

The invention relates to a novel process for the preparation of 1-[3-mercapto-(2S)-methylpropionyl]-pyrrolidine-(2S)-carboxylic acid through the N-acylation of L-proline.

According to the process of the invention L-proline is acylated with a 3-halogen-2-methylpropionyl chloride of the formula III

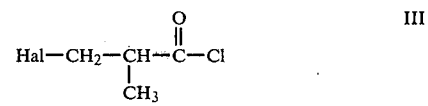

wherein Hal is a halogen atom, preferably chlorine or bromine, the obtained 1-[3-halogen-(2S)-methylpropionyl]-pyrrolidine-(2S)-carboxylic acid, wherein Hal is as stated above, is reacted with an alkali thiosulfate or alkali trithiocarbonate and the reaction product is hydrolized with an acid.

The process of the invention is very economical as compared with the known processes. The desired product is prepared from methacrylic acid in 4 reaction steps with a total yield of 25 percent and from L-proline in 2 reaction steps with a total yield of 30 percent.

6 Claims, No Drawings

PROCESS FOR THE PREPARATION OF 1-[3-MERCAPTO-(2S)-METHYLPROPIONYL]-PYRROLIDINE-(2S)-CARBOXYLIC ACID

The invention relates to a novel process for the preparation of 1-[3-mercapto-(2S)-methylpropionyl]-pyrrolidine-(2S)-carboxylic acid of the formula I

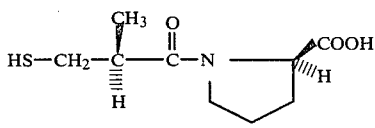

through the acylation of L-proline of the formula IV

The compound of the formula I is an antihypertensive agent inhibiting the angiotensin converting enzyme.

Several possibilities for the preparation of the compound are described in West-German published patent application No. 27 03 828. Thus, L-proline - the carboxylic group of which is optionally protected - is acylated with 3-mercapto-2-methylpropionic acid or a derivative thereof having a protected mercapto group. Either the carboxylic group of L-proline or the mercapto group of the acylating agent must be protected.

In the above published patent application the further possibility is mentioned, in a general way, that L-proline could be acylated with an ω-halogenalkylcarbonyl halide, and the 1-(ω-halogenacyl)-pyrrolidine-2-carboxylic acid formed could be transformed with a thiol or thiocarboxylic acid into a compound of the formula I comprising a protected mercapto group. However, no example has been given for such a reaction, and it also has not been shown how the desired isomer could be isolated.

Since the compound of the formula I has two chiral (i.e. asymmetric) carbon atoms, the number of the possible isomers being formed during the synthesis is equivalent to 4. Even if the starting compound is L-proline, 2 isomers can be formed.

The preparation of the 1-[3-mercapto-(2S)-methylpropionyl]-pyrrolidine-(2S)-carboxylic acid of the formula I is described in more detail in Biochemistry, 16 (25), 5484 (1977).

According to one reaction route, the tert.-butyl ester of L-proline is acylated with 3-acetylthio-2-methylpropionic acid in the presence of N,N'-dicyclohexylcarbodiimide, the product is transformed into its dicyclohexylamine salt and the latter is precipitated with acetonitrile and recrystallized from isopropanol. In this way dicyclohexylamine 1-[3-acetylthio-(2S)-methylpropionyl]-pyrrolidine-(2S)-carboxylate is obtained with a yield of 25 percent. The carboxylic acid is liberated with a yield of 83 percent. Then, the acetyl group protecting the mercapto group is removed by means of ammonia in methanol under a argon atmosphere with a yield of 74 percent. The compound of the formula I is separated as its dicyclohexylamine salt, from which the carboxylic acid is liberated with a yield of 75 percent. The starting tert.-butyl ester of L-proline can be prepared from L-proline in 3 steps (i.e. N-benzyloxycarbonyl-L-proline, yield: 89 percent; tert.-butyl ester of N-benzyloxycarbonyl-L-proline, yield: 93 percent; tert.-butyl ester of L-proline, yield: 77 percent), and the acylating reagent, 3-acetylthio-2-methylpropionic acid can be prepared from methacrylic acid with thioacetic acid with a yield of 83 percent. Thus, the total synthesis consists of 8 reaction steps and the total yield is equivalent to 6.7 percent—calculated for methacrylic acid——and 8.1 percent—calculated for L-proline—, respectively.

According to a further reaction route, L-proline is directly acylated—e.g. according to Schotten and Baumann in the presence of an alkali hydroxide with 3-acetylthio-2-methylpropionyl chloride. The latter reagent is prepared from the corresponding carboxylic acid with a yield of 60 percent. Although the acylation step is performed with a yield of about 95 percent, the dicyclohexylamine 1-[3-acetylthio-(2S)-methylpropionyl]-pyrrolidine-(2S)-carboxylate is obtained merely with a yield of 33 percent, and then follows the purification of the salt from isopropanol. Thus, the total yield of the whole Schotten-Baumann reaction is lower than 30 percent. The carboxylic acid is liberated from the dicyclohexylamine salt with a yield of 83 percent, then the acetyl group protecting the mercapto group is hydrolyzed by means of aqueous ammonia and the compound of the formula I is liberated on a column containing a cation exchanger with a yield of 42 percent.

Although this reaction route consists of only 5 reaction steps, no improvement could be reached regarding the total yield being equivalent to 5.2 percent—calculated for methacrylic acid——and 10.5 percent—calculated for L-proline—, respectively.

None of the known processes insures an economical method that could be performed simply and with an acceptable yield for the preparation of the compound of the formula I.

Therefore, it was the aim of the invention to eliminate the drawbacks connected with the known processes and to provide a process consisting of only a few reaction steps that can be performed economically on an industrial scale, too.

Surprisingly, it has been found that the compound of the formula I can be prepared from L-proline in two reaction steps with a total yield of 30 percent through the acylation of L-proline, if L-proline is acylated with a 3-halogen-2-methylpropionyl chloride of the formula III

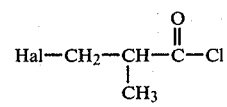

wherein Hal is a halogen atom, preferably chlorine or bromine, the obtained 1-[3-halogen-(2S)-methylpropionyl]-pyrrolidine-(2S)-carboxylic acid of the formula II

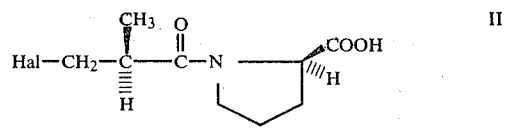

wherein Hal is as stated above, is reacted with an alkali thiosulfate and the reaction product is hydrolyzed with an acid.

L-Proline is acylated according to Schotten and Baumann preferably in aqueous medium at 0° to 25° C. in the presence of an alkali hydroxide, carbonate or hydrogen carbonate. The alkali is employed in an amount corresponding to double the equimolar quantity, in general. Surprisingly, when the reaction mixture is acidified, 1-[3-halogen-(2S)-methylpropionyl]-pyrrolidine-(2S)-carboxylic acid is separated on cooling, the other diastereomer, 1-[3-halogen-(2R)-methylpropionyl]-pyrrolidine-(2S)-carboxylic acid remaining in the aqueous mother liquor.

The 1-[3-halogen-(2S)-methylpropionyl]-pyrrolidine-(2S)-carboxylic acid that can be separated with a yield of 40 percent is a pure and uniform substance, thus, no complicated purification step is required through salt formation with dicyclohexylamine or another base that would result in serious losses.

The other diastereomer remaining in the mother liquor as a by-product can be hydrolyzed to liberate the starting L-proline for reuse in the acylation step.

Of course, the process of the invention can be carried out in such a manner that only the pure 3-halogen-(2S)-methylpropionyl chloride isomer is employed for the acylation of L-proline. In this case only the desired diastereomer is formed.

Preferably, the reaction of the compound of the formula II with alkali thiosulfate is performed in an aqueous medium. The preferred alkali thiosulfate is sodium thiosulfate. The reaction product obtained is a Bunte's salt of the formula V

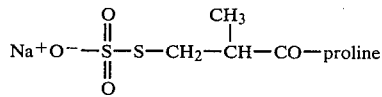

and can be hydrolyzed to give the compound of the formula I. Preferably, the hydrolysis is performed with a mineral acid such as hydrochloric acid. In this way the product of the formula I is obtained from the compound of the formula II with a yield of 70 percent. In general, further purification is not required.

The 3-halogen-2-methylpropionyl chloride employed as acylating agent is prepared as follows:

Methacrylic acid is treated with a hydrogen halide, preferably hydrogen bromide [Cesk. Farm., 24, 112 (1975)], and the 3-bromo-2-methylpropionic acid obtained with a yield of 97 percent is reacted with thionyl chloride to give the acid chloride with a yield of 91 percent [Izv. Acad. Nauk. SSSR, Ser. Chim., 644 (1964)].

The process of the invention is very economical as compared with the known processes. The desired product is prepared from methacrylic acid in 4 reaction steps with a total yield of 25 percent and from L-proline in 2 reaction steps with a total yield of 30 percent. The acylation of L-proline and the transformation of the compound of the formula II can be carried out in an aqueous medium and with a short reaction time. The economics of the process can be further enhanced by regenerating L-proline from the 1-[3-halogen-(2R)-methylpropionyl]-pyrrolidine-(2S)-carboxylic acid formed as by-product.

The invention is further elucidated by means of the following Examples:

EXAMPLE 1

A. 1-[3-Bromo-(2S)-methylpropionyl]-pyrrolidine-(2S)-carboxylic acid 8.28 g (0.072 moles) of L-proline are added to a solution of 2.88 g (0.072 moles) of sodium hydroxide in 35 ml of water. To the solution obtained, 13.34 g (0.072 moles) of 3-bromo-2-methylpropionyl chloride and a solution of 2.88 g (0.072 moles) of sodium hydroxide in 35 ml of water are added, simultaneously, at 0° to 5° C. The two additions are carried out at a rate to ensure that the temperature of the reaction mixture should not exceed +10° C., and both additions should be finished nearly at the same time. Cooling is stopped and the reaction mixture is stirred for an additional 6 hours, then left to stand for 12 hours.

The mixture is extracted with 15 ml of ether and acidified with 37 percent hydrochloric acid to a pH value of 2 under ice cooling. The product separating as a colorless oil becomes crystalline in an hour. It is filtered and washed with some ice water.

11.1 g of white crystals obtained (m.p. 67°–72° C.) are recrystallized from 44 ml of water to give 8.0 g /40%/ of 1-[3-bromo-(2S)-methylpropionyl]-pyrrolidine-(2S)-carboxylic acid monohydrate, m.p. 71°–74° C. $[\alpha]_D^{20} = -89°$ (c=1; ethanol).

When dried over phosphorus pentoxide at 20 mm Hg for 1 hour, the anhydrous compound is obtained, m.p. 110°–114° C. $[\alpha]_D^{20} = -94.9°$ (c=1; ethanol).

The mother liquors of the (S-S) isomers are combined, extracted with chloroform three times, the organic phases are dried, evaporated, the residue is crystallized with carbon tetrachloride and recrystallized from a 50-fold quantity of ether. 1-[3-Bromo-(2R)-methylpropionyl]-pyrrolidine-(2S)-carboxylic acid is obtained, m.p. 102°–104° C. $[\alpha]_D^{20} = -33.5°$ (c=1; ethanol).

B. 1-[3-Mercapto-(2S)-methylpropionyl]-pyrrolidine-(2S)-carboxylic acid 14.1 g (0.050 moles) of 1-[3-bromo-(2S)-methylpropionyl]-pyrrolidine-(2S)-carboxylic acid are dissolved in a solution of 4.4 g (0.053 moles) of sodium hydrogen carbonate in 100 ml of water. To the solution obtained, 13.0 g (0.053 moles) of crystalline sodium thiosulfate ($Na_2S_2O_3 \cdot 5H_2O$) are added. The mixture is refluxed for an hour, then cooled, acidified with 20 ml of 37 percent hydrochloric acid, refluxed again for an hour and cooled to 20° C.

The mixture is extracted with ethyl acetate three times, the organic phases are combined, washed with 40 ml of saturated aqueous sodium chloride solution, dried over anhydrous magnesium sulfate and evaporated. The colorless, oily residue is dissolved in 40 ml of hot ethyl acetate, filtered and the product is precipitated with n-hexane.

7.0 g (70%) of white crystalline 1-[3-mercapto-(2S)-methylpropionyl]-pyrrolidine-(2S)-carboxylic acid are obtained, m.p. 103°–105° C. $[\alpha]_D^{22} = -130.3°$ (c=1.7; ethanol).

Preparation of the starting compound:

3-Bromo-2-methylpropionyl chloride

A. 3-Bromo-2-methylpropionic acid 86 ml (1.01 moles) of methacrylic acid are dissolved in 80 ml of chloroform and hydrogen bromide is bubbled into the solution at −10° C. under stirring. After the absorption of the calculated quantity of gaseous hydrogen bromide, the solution is left to stand at 0° C. for 12 hours. The chloroform is evaporated and the residue is distilled in vacuo.

164.8 g (97.3%) of 3-bromo-2-methylpropionyl chloride are obtained, b.p. 101°-104° C./7 mm Hg. $n_D^{24.5} = 1.4753$.

B. 3-Bromo-2-methylpropionyl chloride

The mixture of 125.0 g (0.75 moles) of 3-bromo-2-methylpropionic acid and 150 ml of thionyl chloride is heated at 70° C. for 6 hours, then the thionyl chloride is evaporated at 40 mm Hg. and the residue is distilled at 8 mm Hg.

126.8 g (91.4%) of 3-bromo-2-methylpropionyl chloride are obtained, b.p. 40°-41° C./8 mm Hg. $n_D^{23} = 1.4815$.

What we claim is:

1. A process for the preparation of 1-[3-mercapto-(2S)-methyl-propionyl]-pyrrolidine-(2S)-carboxylic acid of the formula (I)

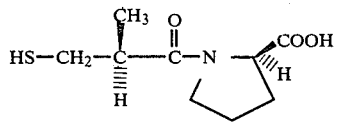

which comprises the steps of:

(a) N-acylating L-proline of the formula (IV)

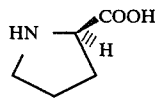

with a 3-halo-2-methyl-propionyl chloride of the formula (III)

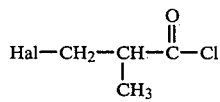

wherein Hal is a halogen atom, in an aqueous medium at a temperature of 0° to 25° C. in the presence of an alkali selected from the group consisting of an alkali hydroxide, alkali carbonate and an alkali bicarbonate, wherein the alkali is present in a molar amount double the amount of the compound of the formula (III) or of the compound of the formula (IV) to form an aqueous mixture of a 1-[3-halo-(2S)-methylpropionyl]-pyrrolidine-(2S)-carboxylic acid of the formula (II)

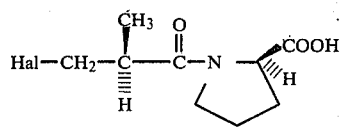

and its diastereomer 1-[3-halo-(2R)-methyl-propionyl]-pyrrolidine-(2S)-carboxylic acid;

(b) acidifying the aqueous mixture formed during step (a) under ice cooling to form crystals of 1-[3-halo-(2S)-methylpropionyl]-pyrrolidine-(2S)-carboxylic acid while 1-[3-halo-(2R)-methyl-propionyl]-pyrrolidine-(2S)-carboxylic acid remains in solution;

(c) separating the crystals of the 1-[3-halo-(2S)-methylpropionyl]-pyrrolidine-(2S)-carboxylic acid from the solution containing the 1-[3-halo-(2R)-methylpropionyl]-pyrrolidine-(2S)-carboxylic acid;

(d) [treating the 1-[3-halo-(2S)-methyl-propionyl]-pyrrolidine-(2S)-methylpropionyl]-pyrrolidine-(2S)-carboxylic acid with an alkali thiosulfate to form a compound of the formula (V)

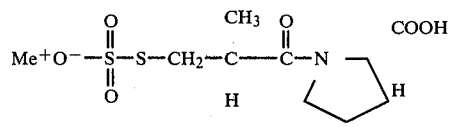

wherein Me is an alkali metal; and (e) hydrolyzing the compound of the formula (V) with an acid to form the compound of the formula (I).

2. The process defined in claim 1, step (d), wherein the alkali thiosulfate is sodium thiosulfate.

3. The process defined in claim 1, step (e), wherein the acid is hydrochloric acid.

4. The process defined in claim 1 wherein the 1-[3-halo-(2R)-methylpropionyl]-pyrrolidine-(2S)-carboxylic acid separated during step (c) is hydrolyzed to liberate L-proline of the formula (IV) to be used during step (a).

5. A salt of the formula (V)

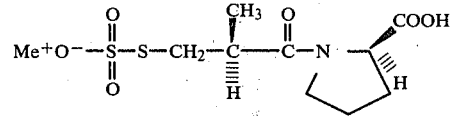

wherein Me is an alkali metal.

6. The salt defined in claim 5 wherein Me is sodium.

* * * * *